(12) United States Patent
Distler et al.

(10) Patent No.: US 9,561,317 B2
(45) Date of Patent: Feb. 7, 2017

(54) SYSTEM AND METHOD FOR DELIVERING A TARGET VOLUME OF FLUID

(71) Applicant: DEKA Products Limited Partnership, Manchester, NH (US)

(72) Inventors: Carl R. Distler, Huntsville, AL (US); Gregory L. Distler, Huntsville, AL (US); Jason A. Demers, Manchester, NH (US); Geoffrey P. Spencer, Manchester, NH (US); Robert J. Bryant, Jr., Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 68 days.

(21) Appl. No.: 14/297,219

(22) Filed: Jun. 5, 2014

(65) Prior Publication Data

US 2014/0288490 A1     Sep. 25, 2014

Related U.S. Application Data

(60) Continuation of application No. 11/926,700, filed on Oct. 29, 2007, now Pat. No. 8,821,475, which is a
(Continued)

(51) Int. Cl.
| | |
|---|---|
| *A61M 1/28* | (2006.01) |
| *A61M 39/22* | (2006.01) |
| *A61M 5/168* | (2006.01) |

(52) U.S. Cl.
CPC ............ *A61M 1/282* (2014.02); *A61M 1/28* (2013.01); *A61M 1/281* (2014.02);
(Continued)

(58) Field of Classification Search
CPC ........ A61M 1/282; A61M 1/281; A61M 1/28; A61M 2210/1017; A61M 1/288; A61M 5/16827; A61M 5/16804; A61M 5/16881; A61M 5/31573; A61M 5/142
See application file for complete search history.

(56) References Cited

U.S. PATENT DOCUMENTS

| | | |
|---|---|---|
| 2,339,876 A | 1/1944 | Phillips |
| 3,083,943 A | 4/1963 | Stewart et al. |
| (Continued) | | |

FOREIGN PATENT DOCUMENTS

| | | |
|---|---|---|
| DE | 19704564 A1 | 8/1998 |
| EP | 0 013 334 A2 | 7/1980 |
| (Continued) | | |

OTHER PUBLICATIONS

Office Action for U.S. Appl. No. 10/412,658, filed Apr. 10, 2003, published as US 2003-0220627 on Nov. 27, 2003, which Office Action is dated Aug. 25, 2006, and claims as pending for U.S. Appl. No. 10/412,658 as of Aug. 25, 2006.
(Continued)

*Primary Examiner* — Imani Hayman
*Assistant Examiner* — Nilay Shah
(74) *Attorney, Agent, or Firm* — Wolf, Greenfield & Sacks, P.C.

(57) ABSTRACT

A method for delivering a target volume of fluid to a destination is provided. The method includes delivering a first volume of fluid to the destination in increments each having approximately a first incremental volume, the first volume of fluid being less than the target volume and delivering a second volume of fluid to the destination in increments each having approximately a second incremental volume, the second incremental volume being less than the first incremental volume, such that the sum of the first volume and the second volume is approximately equal to the target volume.

60 Claims, 5 Drawing Sheets

Related U.S. Application Data division of application No. 10/412,658, filed on Apr. 10, 2003, now Pat. No. 7,544,179.

(60) Provisional application No. 60/371,894, filed on Apr. 11, 2002.

(52) U.S. Cl.
CPC ........ *A61M 5/16827* (2013.01); *A61M 39/22* (2013.01); *A61M 5/16804* (2013.01); *A61M 5/16831* (2013.01); *A61M 5/16881* (2013.01); *A61M 2205/123* (2013.01); *A61M 2205/128* (2013.01); *A61M 2205/3396* (2013.01); *A61M 2210/1017* (2013.01)

(56) References Cited

U.S. PATENT DOCUMENTS

| | | |
|---|---|---|
| 3,656,873 A | 4/1972 | Schiff |
| RE27,849 E | 12/1973 | Wortman |
| 4,222,127 A | 9/1980 | Donachy et al. |
| 4,381,545 A * | 4/1983 | Biddle, III ......... G01G 13/2852 141/128 |
| 4,637,817 A | 1/1987 | Archibald et al. |
| 4,666,598 A | 5/1987 | Heath et al. |
| 4,695,385 A | 9/1987 | Boag |
| 4,705,506 A | 11/1987 | Archibald |
| 4,778,451 A | 10/1988 | Kamen |
| 4,826,482 A | 5/1989 | Kamen |
| 4,863,461 A | 9/1989 | Jarvik |
| 4,966,579 A | 10/1990 | Polaschegg |
| 4,971,700 A | 11/1990 | Tsuji et al. |
| 4,976,162 A | 12/1990 | Kamen |
| 4,976,729 A | 12/1990 | Holfert et al. |
| 4,997,570 A | 3/1991 | Polaschegg |
| 5,024,756 A | 6/1991 | Sternby |
| 5,088,515 A | 2/1992 | Kamen |
| 5,098,262 A | 3/1992 | Wecker et al. |
| 5,178,182 A | 1/1993 | Kamen |
| 5,242,384 A | 9/1993 | Robinson et al. |
| 5,247,434 A | 9/1993 | Peterson et al. |
| 5,324,422 A * | 6/1994 | Colleran ................. A61M 1/28 210/143 |
| 5,349,896 A | 9/1994 | Delaney, III et al. |
| 5,350,357 A | 9/1994 | Kamen et al. |
| 5,421,823 A | 6/1995 | Kamen et al. |
| 5,438,510 A | 8/1995 | Bryant et al. |
| 5,476,368 A | 12/1995 | Rabenau et al. |
| 5,487,827 A | 1/1996 | Peterson et al. |
| 5,507,412 A | 4/1996 | Ebert et al. |
| 5,586,438 A | 12/1996 | Fahy |
| 5,634,896 A | 6/1997 | Bryant et al. |
| 5,645,531 A | 7/1997 | Thompson et al. |
| 5,676,645 A | 10/1997 | Van Waeg et al. |
| 5,744,027 A | 4/1998 | Connell et al. |
| 5,906,978 A * | 5/1999 | Ash ........................ A61K 33/26 424/648 |
| 5,925,011 A * | 7/1999 | Faict ................... A61M 1/1656 222/145.5 |
| 5,925,014 A | 7/1999 | Teeple Jr. |
| 5,989,423 A | 11/1999 | Kamen et al. |
| 6,041,801 A | 3/2000 | Gray et al. |
| 6,223,130 B1 | 4/2001 | Gray et al. |
| 6,277,272 B1 | 8/2001 | Nikaido et al. |
| 6,284,131 B1 | 9/2001 | Hogard et al. |
| 6,295,918 B1 | 10/2001 | Simmons et al. |
| 6,327,895 B1 | 12/2001 | Jeppsson et al. |
| 6,382,923 B1 | 5/2002 | Gray |
| 6,503,062 B1 | 1/2003 | Gray et al. |
| 6,604,908 B1 | 8/2003 | Bryant et al. |
| 6,649,063 B2 | 11/2003 | Brugger et al. |
| 6,749,403 B2 | 6/2004 | Bryant et al. |
| 6,758,975 B2 | 7/2004 | Peabody et al. |
| 6,821,441 B2 | 11/2004 | Pedrini et al. |
| 6,877,419 B2 | 4/2005 | Ohrle et al. |
| 6,905,479 B1 | 6/2005 | Bouchard et al. |
| 6,953,323 B2 | 10/2005 | Childers et al. |
| 7,029,245 B2 | 4/2006 | Maianti et al. |
| 7,041,076 B1 | 5/2006 | Westberg et al. |
| 7,238,164 B2 | 7/2007 | Childers et al. |
| 7,300,413 B2 | 11/2007 | Burbank et al. |
| 7,524,417 B2 | 4/2009 | Sunohara et al. |
| 7,544,179 B2 | 6/2009 | Distler et al. |
| 7,559,524 B2 | 7/2009 | Gray et al. |
| 7,575,564 B2 | 8/2009 | Childers |
| 7,648,627 B2 | 1/2010 | Beden et al. |
| 7,776,006 B2 | 8/2010 | Childers et al. |
| 7,794,141 B2 | 9/2010 | Perry et al. |
| 7,892,197 B2 | 2/2011 | Folden et al. |
| 8,002,726 B2 | 8/2011 | Karoor et al. |
| 8,029,454 B2 | 10/2011 | Kelly et al. |
| 8,105,265 B2 | 1/2012 | Demers et al. |
| 8,197,439 B2 | 6/2012 | Wang et al. |
| 8,211,048 B2 | 7/2012 | Szamosfalvi et al. |
| 8,292,594 B2 | 10/2012 | Tracey et al. |
| 8,357,298 B2 | 1/2013 | Demers et al. |
| 8,409,441 B2 | 4/2013 | Wilt et al. |
| 8,459,292 B2 | 6/2013 | Wilt et al. |
| 8,512,553 B2 | 8/2013 | Cicchello et al. |
| 8,597,229 B2 | 12/2013 | Pan |
| 8,673,139 B2 | 3/2014 | Hedmann et al. |
| 8,721,879 B2 | 5/2014 | Van der Merwe et al. |
| 8,821,475 B2 | 9/2014 | Distler et al. |
| 8,821,476 B2 | 9/2014 | Agah et al. |
| 8,858,787 B2 | 10/2014 | Muller et al. |
| 8,870,549 B2 | 10/2014 | Tracey et al. |
| 8,870,812 B2 | 10/2014 | Alberti et al. |
| 8,968,232 B2 | 3/2015 | Kamen et al. |
| 9,115,708 B2 | 8/2015 | Van der Merwe et al. |
| 2002/0072733 A1 | 6/2002 | Flaherty |
| 2002/0103453 A1 | 8/2002 | Burbank et al. |
| 2003/0194328 A1 | 10/2003 | Bryant et al. |
| 2003/0194332 A1 | 10/2003 | Jahn et al. |
| 2003/0220607 A1 | 11/2003 | Busby et al. |
| 2003/0220627 A1 | 11/2003 | Distler et al. |
| 2003/0230191 A1 | 12/2003 | Ohrle et al. |
| 2004/0001766 A1 | 1/2004 | Maianti et al. |
| 2004/0009096 A1 | 1/2004 | Wellman |
| 2005/0045540 A1 | 3/2005 | Connell et al. |
| 2005/0100450 A1 | 5/2005 | Bryant et al. |
| 2005/0145010 A1 | 7/2005 | Vanderveen et al. |
| 2005/0209563 A1 | 9/2005 | Hopping et al. |
| 2008/0058697 A1 | 3/2008 | Kamen et al. |
| 2008/0114330 A1 | 5/2008 | Distler et al. |
| 2008/0175719 A1 | 7/2008 | Tracey et al. |
| 2010/0133153 A1 | 6/2010 | Beden et al. |
| 2010/0185134 A1 | 7/2010 | Houwen et al. |
| 2011/0005992 A1 | 1/2011 | Kelly et al. |
| 2011/0009797 A1 | 1/2011 | Kelly et al. |
| 2011/0092893 A1 | 4/2011 | Demers et al. |
| 2011/0303588 A1 | 12/2011 | Kelly et al. |
| 2011/0303598 A1 | 12/2011 | Lo et al. |
| 2013/0193041 A1 | 8/2013 | Rohde |
| 2013/0304020 A1 | 11/2013 | Wilt et al. |
| 2014/0112828 A1 | 4/2014 | Grant et al. |
| 2014/0288488 A1 | 9/2014 | Distler et al. |
| 2014/0288489 A1 | 9/2014 | Distler et al. |
| 2014/0299544 A1 | 10/2014 | Wilt et al. |
| 2014/0309611 A1 | 10/2014 | Wilt et al. |
| 2014/0322053 A1 | 10/2014 | van der Merwe et al. |
| 2015/0050166 A1 | 2/2015 | Tracey et al. |
| 2015/0196699 A9 | 7/2015 | Wilt et al. |
| 2016/0030657 A1 | 2/2016 | Kelly et al. |
| 2016/0030658 A1 | 2/2016 | van der Merwe et al. |
| 2016/0058933 A1 | 3/2016 | Ballantyne et al. |
| 2016/0101227 A1 | 4/2016 | Norris et al. |
| 2016/0101278 A1 | 4/2016 | Norris et al. |
| 2016/0144093 A1 | 5/2016 | Demers et al. |

(56) References Cited

U.S. PATENT DOCUMENTS

| | | |
|---|---|---|
| 2016/0175505 A1 | 6/2016 | Demers et al. |
| 2016/0175506 A1 | 6/2016 | Wilt et al. |

FOREIGN PATENT DOCUMENTS

| | | |
|---|---|---|
| EP | 0 288 145 A1 | 10/1988 |
| EP | 1 362 604 A1 | 11/2003 |
| GB | 1 508 116 A | 4/1978 |
| JP | S60-077782 U | 5/1985 |
| JP | S62-5355 A | 1/1987 |
| JP | H09-099060 | 4/1997 |
| JP | H11-210633 A | 8/1999 |
| JP | 2003-509131 | 3/2003 |
| JP | 3422023 | 6/2003 |
| JP | 2003-265599 A | 9/2003 |
| JP | 2006-204343 A | 8/2006 |
| JP | 2008-104737 A | 5/2008 |
| KR | 10-2002-0008145 | 1/2002 |
| WO | WO 84/02473 A1 | 7/1984 |
| WO | WO 93/11829 | 6/1993 |
| WO | WO 97/05913 A1 | 2/1997 |
| WO | WO 00/57935 | 10/2000 |
| WO | WO 01/19430 A1 | 3/2001 |
| WO | WO 2007/120812 A2 | 10/2007 |
| WO | WO 2009/094183 A1 | 7/2009 |
| WO | WO 2013/067359 A2 | 5/2013 |

OTHER PUBLICATIONS

Office Action for U.S. Appl. No. 10/412,658, filed Apr. 10, 2003, published as US 2003-0220627 on Nov. 27, 2003, which Office Action is dated Feb. 27, 2007, and claims as pending for U.S. Appl. No. 10/412,658 as of Feb. 27, 2007.

Office Action for U.S. Appl. No. 10/412,658, filed Apr. 10, 2003, published as US 2003-0220627 on Nov. 27, 2003, which Office Action is dated Aug. 9, 2007, and claims as pending for U.S. Appl. No. 10/412,658 as of Aug. 9, 2007.

Office Action for U.S. Appl. No. 10/412,658, filed Apr. 10, 2003, published as US 2003-0220627 on Nov. 27, 2003, which Office Action is dated May 14, 2008, and claims as pending for U.S. Appl. No. 10/412,658 as of May 14, 2008.

Office Action for U.S. Appl. No. 11/926,700, filed Oct. 29, 2007, published as US 2008-0114330 on May 15, 2008, which Office Action is dated Jan. 4, 2011, and claims as pending for U.S. Appl. No. 11/926,700 as of Jan. 4, 2011.

Office Action for U.S. Appl. No. 11/926,700, filed Oct. 29, 2007, published as US 2008-0114330 on May 15, 2008, which Office Action is dated Feb. 15, 2012, and claims as pending for U.S. Appl. No. 11/926,700 as of Feb. 15, 2012.

Office Action for U.S. Appl. No. 11/926,700, filed Oct. 29, 2007, published as US 2008-0114330 on May 15, 2008, which Office Action is dated Nov. 29, 2013, and claims as pending for U.S. Appl. No. 11/926,700 as of Nov. 29, 2013.

Bengtsson etal., Haemo dialysis software architecture design experiences. Proceeedings of the 1999 International Conferene on Software Engineering. IEEE Cat. No. 99CB37002. New York, NY. 1999:516-25.

Gentilini et al., Automatic controllers capable of regulating mutliple patient outputs for higher-quality anesthesia treatment. IEEE Engineering in Medicine and Biology Magazine. IEEE Service Centers. Piscataway, NJ. Jan. 1, 2001;20(1):39-53.

Office Action for U.S. Appl. No. 14/297,183, filed Jun. 5, 2014, published as US 2014-0288488 on Sep. 25, 2014, which Office Action is dated Jan. 21, 2016, and claims as pending for U.S. Appl. No. 14/297,183 as of Jan. 21, 2016.

Office Action for U.S. Appl. No. 14/297,235, filed Jun. 5, 2014, published as US 2014-0288489 on Sep. 25, 2014, which Office Action is dated Jan. 29, 2016, and claims as pending for U.S. Appl. No. 14/297,235 as of Jan. 29, 2016.

Office Action for U.S. Appl. No. 14/297,183, filed Jun. 5, 2014, published as 2014-0288488 on Sep. 25, 2014, which Office Action is dated Sep. 28, 2016, and claims as pending for US pending for U.S. Appl. No. 14/297,183 as of Sep. 28, 2016.

Notice of Allowance for U.S. Appl. No. 14/297,235, filed Jun. 5, 2014, published as 2014-0288489 on Sep. 25, 2014, which Notice of Allowance is dated Sep. 28, 2016, and claims as pending for U.S. Appl. No. 14/297,235 as of Sep. 28, 2016.

* cited by examiner

SYSTEM AND METHOD FOR DELIVERING A TARGET VOLUME OF FLUID

CROSS-REFERENCE TO RELATED APPLICATIONS

This application is a continuation of U.S. application Ser. No. 11/926,700 filed Oct. 29, 2007 and issued on Sep. 2, 2014 as U.S. Pat. No. 8,821,475, which is a divisional of U.S. application Ser. No. 10/412,658 filed on Apr. 10, 2003, now issued as U.S. Pat. No. 7,544,179 on Jun. 9, 2009, herein incorporated by reference, which claims priority from U.S. Provisional Application Ser. No. 60/371,894 which is hereby incorporated herein by reference.

TECHNICAL FIELD AND BACKGROUND ART

The present invention relates to fluid delivery systems, and in particular to systems and methods for accurately delivering a target volume of fluid to a destination.

Such systems regulate the rate of flow of fluid through a line. Some examples of fluid delivery systems are peritoneal dialysis machines and intravenous fluid delivery systems. These systems may include a permanent housing which does not come into direct contact with the transporting fluid and into which a fluid-exposed disposable cassette is placed. The disposable cassette includes flexible membranes, or other structures that respond to pressure and that separate the permanent components from the fluid being delivered. Examples of such fluid delivery systems and their sub-components (e.g., pressure conduction chambers, flow measurement systems and valves) are disclosed in U.S. Pat. Nos. 4,778,451, 4,826,482, 4,976,162, 5,088,515, 5,178,182 issued to Kamen, U.S. Pat. No. 5,989,423 issued to Kamen et al. and U.S. Pat. No. 6,503,062 issued to Gray et al. These patents are all hereby incorporated herein by reference.

One problem with respect to fluid delivery systems, such as in peritoneal dialysis, arises when treating subjects with low fill volume capacities, such as a child. For example, in peritoneal dialysis systems, a fill volume of 1000 mL or less generally indicates a low fill volume while fill volumes of greater than 1000 mL are typical for an average adult's fill volume. Thus, a single fluid delivery system may not be appropriate for treating both an average adult and a child.

Another problem arises with respect to fluid delivery systems when two or more fluids from two or more sources must be delivered to a subject or patient simultaneously and in a particular ratio. It is difficult to maintain a consistent ratio of the different fluids for simultaneous delivery to the subject because each source may deliver its solution to the system at different rates and/or in different volumes. Consequently, it is difficult to maintain a consistent ratio of the different fluids in the fluid delivery system at any one time.

SUMMARY OF THE INVENTION

In a first embodiment of the invention, a method for delivering a target volume of fluid to a destination includes delivering a first volume of fluid to the destination in increments each having approximately a first incremental volume, the first volume of fluid being less than the target volume. A second volume of fluid is then delivered to the destination in increments each having approximately a second incremental volume. The second incremental volume is less than the first incremental volume, and the sum of the first volume and the second volume is approximately equal to the target volume.

Delivering the first and second volumes of fluid to a destination may include delivering the first and second volumes of fluid parenterally to a human subject. Similarly, delivering the first and second volumes of fluid to a destination may include delivering the first and second volumes of fluid to a fluid reservoir and/or delivering the first and second volumes of fluid to a container. Such a container may be a heating bag, such as may be used in conjunction with a peritoneal dialysis system, and/or a pump chamber. In accordance with a related embodiment, the first volume may be approximately equal to the target volume minus a finish volume and the second incremental volume may be less than the finish volume. In a related embodiment, the second incremental volume may be less than one third the finish volume.

In accordance with another embodiment of the invention, a system for delivering a target volume of fluid to a destination includes a fluid control module for delivering a first volume of fluid to the destination in increments each having approximately a first incremental volume, the first volume of fluid being less than the target volume. The fluid control module also delivers a second volume of fluid to the destination in increments each having approximately a second incremental volume, the second incremental volume being less than the first incremental volume. The sum of the first volume and the second volume is approximately equal to the target volume. The system also includes a valve arrangement for controlling fluid communication to the destination and a controller for determining the volume of fluid delivered to the destination and for controlling the valve arrangement and the fluid control module. The fluid control module may deliver the first and second volumes of fluid to a human subject and the first and second volumes of fluid may be delivered parenterally. Similarly, the fluid control module may deliver the first and second volumes of fluid to a fluid reservoir and/or a container such as a heating bag and/or a pump chamber.

In accordance with related embodiments, the first volume may be approximately equal to the target volume minus a finish volume and the second incremental volume may be less than the finish volume. For example, the second incremental volume may be less than one third the finish volume.

In accordance with a further embodiment of the invention, a method for simultaneously delivering a target volume of fluid from two sources in a desired ratio to a common destination includes delivering a first volume of fluid from a first source and a second volume of fluid from a second source to the destination in increments each having approximately a first incremental volume, the first incremental volume of fluid being substantially less than the target volume. After delivery of a first incremental volume of fluid from the first source and the second source, the volume of fluid delivered to the destination from the first source and the volume of fluid delivered to the destination from the second source is measured. Delivery of the first volume of fluid to the destination is suspended when the first volume exceeds the second volume by a fraction, which may be a predetermined fraction, of the first incremental volume. A first incremental volume of fluid from the second source is delivered to the destination, and delivery of the first volume of fluid to the destination is resumed.

In accordance with related embodiments, the first incremental volume of fluid may be less than one quarter of the target volume. In accordance with further related embodiments, the desired ratio may be 1:1 and the predetermined fraction may be one half. Delivering the first and second volumes of fluid to a destination may include delivering the first and second volumes of fluid parenterally to a human subject. Similarly, delivering the first volume and second volumes of fluid to a destination may include delivering the first and second volumes of fluid to a fluid reservoir and/or container, and such a container may be a heating bag and/or a pump chamber.

In accordance with other related embodiments, the method may include determining that approximately the target volume of fluid has been delivered to the destination and measuring the volume of fluid delivered to the destination from the first source and the volume of fluid delivered to the destination from the second source. A third volume of fluid from the source that has delivered a smaller volume of fluid to the destination may then be delivered in increments each having approximately a second incremental volume, the second incremental volume being less than the first incremental volume, such that the volume of fluid delivered to the destination from the first source and the volume of fluid delivered from the second source are in approximately the desired ratio. The sum of the first volume and the second volume may be approximately equal to the target volume minus a finish volume, and the second incremental volume may be less than the finish volume. In one related embodiment, the second incremental volume is less than one third the finish volume.

In accordance with another embodiment of the invention, a system for simultaneously delivering a target volume of fluid from two sources in a desired ratio to a common destination includes a first fluid source, a second fluid source, and a fluid control module. The fluid control module delivers a first volume of fluid from the first fluid source and a second volume of fluid from the second fluid source to the destination in increments each having approximately a first incremental volume, the first incremental volume being substantially less than the target volume. The fluid control module also measures the volume of fluid delivered to the destination from the first source and the volume of fluid delivered to the destination from the second source, suspends delivery of the first volume of fluid to the destination when the first volume exceeds the second volume by a fraction, which may be a predetermined fraction, of the first incremental volume, and resumes delivery of the first volume of fluid to the destination. The system also includes a valve arrangement for controlling fluid communication between the destination and first and second fluid sources and a controller for determining the first and second volumes of fluid, the first incremental volume of fluid, and for controlling the valve arrangement and the fluid control module.

In accordance with related embodiments, the first incremental volume may be less than one quarter of the target volume. Additionally, the desired ratio may be 1:1 and the predetermined fraction may be approximately one half. In accordance with yet further related embodiments, the fluid control module may deliver the first and second volumes of fluid to a human subject, and the fluid control module may deliver the first and second volumes of fluid parenterally. Similarly, the fluid control module may deliver the first and second volumes of fluid to a fluid reservoir and/or to a container. Such a container may be a heating bag and/or a pump chamber. The controller may also determine that approximately the target volume minus a finish volume of fluid has been delivered to the destination. Further, the fluid control module may measure the volume of fluid delivered to the destination from the first source and the volume of fluid delivered to the destination from the second source and deliver a third volume of fluid from the source that has delivered a smaller volume of fluid to the destination. The third volume of fluid may be delivered in increments each having approximately a second incremental volume. The second incremental volume may be less than the first incremental volume, such that the volume of fluid delivered to the destination from the first source and the volume of fluid delivered from the second source are in approximately the desired ratio. Further, the sum of the first and the second volumes may be approximately equal to the target volume minus a finish volume and the second incremental volume may be less than the finish volume. For example, the second incremental volume may be less than one third the finish volume.

In accordance with a further embodiment of the invention, a system for delivering a target volume of fluid to a destination includes fluid delivery means for delivering a first volume of fluid to the destination in one or more first incremental volumes, the first volume of fluid being less than the target volume, and delivering a second volume of fluid to the destination in one or more second incremental volumes, the second incremental volume being less than the first incremental volume. The system also includes measuring means for measuring the volume of fluid delivered to the destination and control means for controlling the fluid delivery means.

In accordance with another embodiment of the invention, a system for simultaneously delivering a target volume of fluid from two sources in a desired ratio to a common destination includes a first fluid source and a second fluid source. Fluid delivery means delivers a first volume of fluid from the first fluid source and a second volume of fluid from the second fluid source to the destination in one or more first incremental volumes, the first incremental volume being substantially less than the target volume. Measuring means measures the volume of fluid delivered to the destination from the first source and the volume of fluid delivered to the destination from the second source. Control means suspends delivery of the first volume of fluid to the destination when the first volume exceeds the desired ratio with respect to the second volume by a fraction, which may be a predetermined fraction, of the first incremental volume and then resumes delivery of the first volume of fluid to the destination.

In accordance with a further embodiment of the invention, a system for simultaneously delivering a target volume of fluid from two sources in a desired ratio to a common destination includes a first fluid source and a second fluid source. The system also includes fluid delivery means for delivering a first volume of fluid from the first fluid source and a second volume of fluid from the second fluid source to the destination in one or more first incremental volumes, the first incremental volume being substantially less than the target volume, and measuring means for measuring the volume of fluid delivered to the destination from the first source and the volume of fluid delivered to the destination from the second source. The control means suspends delivery of the first volume of fluid to the destination when the first volume exceeds the second volume by a fraction, which may be a predetermined fraction, of the first incremental volume and resumes delivery of the first volume of fluid to the destination. In accordance with related embodiments, the desired ratio may be 1:1 and the predetermined fraction may be approximately one half.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
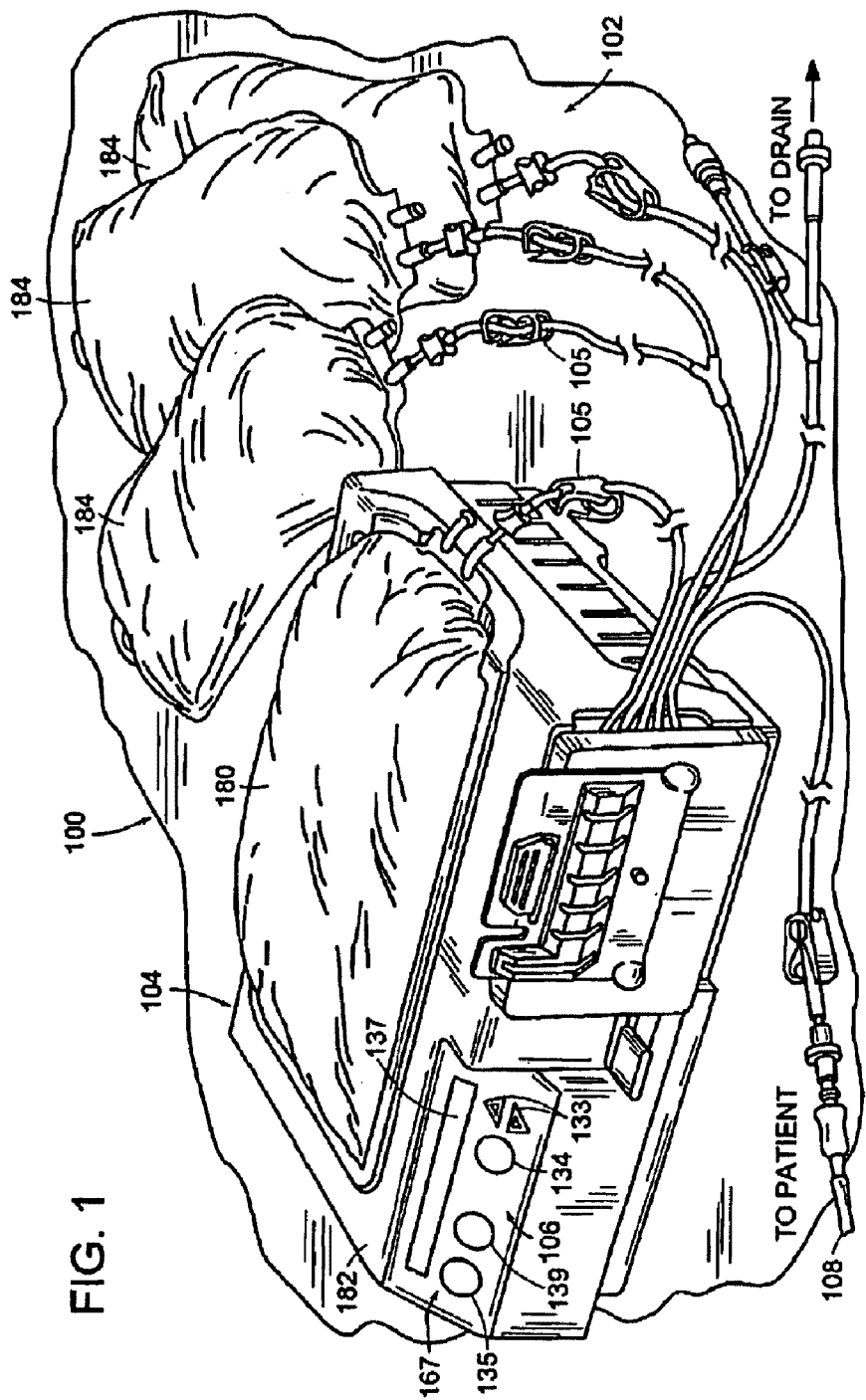
FIG. 1 is a perspective view of an automated fluid delivery system that may be used in conjunction with the present invention.

FIG. 1 is a perspective view of an automated fluid management system that may be used in conjunction with the present invention. The system 100 includes a liquid supply and delivery set 102, a fluid control module 104 that interacts with the delivery set 102 to pump liquid through it, and a controller 106 that governs the interaction to perform a selected procedure. In the depicted embodiment, the fluid control module and controller are located within a common housing 182.

The fluid control module 104 utilizes a pneumatic pumping action to emulate gravity flow, regardless of the position of the source solution bags 184. The pumping action may be the result of pressurizing one or more fluid chambers through use of a control gas or liquid, or other methods known in the art, such as pumps, pistons, piezo-electric mechanisms, pressurized reservoirs, valves, clamps and vents. As noted above, these pressurizing devices are explained in greater detail in the patents referenced above and incorporated herein by reference.

The controller 106 carries out process control and monitoring functions for the fluid control module 104. The controller includes a user interface 167 with a display screen 137 and control pad. The interface 167 presents menus, sub-menus and status information to the user during a therapy session. The interface 167 also allows the user to enter and edit therapy parameters, and to issue therapy commands. In one embodiment, the user interface 167 receives characters from a keypad, displays text to the display screen 137 and sounds an alarm when appropriate. The control pad may include a "Go" key 135, which when pressed causes the interface 167 to display a main menu on the display screen 137 for initiating a therapy session, and a "Stop" key 139 which when pressed causes a therapy session to cease. The interface 167 may also include keys 133 for traversing through the information and menus displayed on the display screen 137 and an "Enter" key 134 for causing data to be input to the system or for selecting an entry from the menus.

In the illustrated embodiment, the controller 106 comprises a central processing unit. The central processing unit may employ conventional real time multi-tasking to allocate tasks. The central processing unit may itself be programmable or alternatively, it may run under the direction of a software, middle-ware or hardware program external to the system.

In use, for example as a peritoneal dialysis system, the user connects the set 102 to his/her indwelling peritoneal catheter 108. The user also connects the set 102 to individual bags 184 containing peritoneal dialysis solution for infusion. The set 102 also connects to a heating bag 180 in which the dialysis solution is heated to a desired temperature. In accordance with an embodiment of the invention described in more detail below, two or more fluids from different sources may be simultaneously pumped to the heating bag in a desired ratio.

The controller 106 paces the fluid control module 104 through a prescribed series of fill, dwell, and drain phases typical of an automated peritoneal dialysis procedure. During the fill phase, the fluid control module 104 infuses the heated solution through the set 102 and into the patient's peritoneal cavity. Following the dwell phase, the fluid control module 104 institutes a drain phase, during which the fluid control module 104 discharges spent dialysis solution from the patient's peritoneal cavity through the set into a nearby drain.

The delivery set 102 includes a cassette (not visible) which mounts inside a holder in the fluid control module 104. The cassette serves in association with the fluid control module 104 and the controller to direct liquid flow among multiple fluid sources and destinations that an automatic peritoneal dialysis procedure requires. The cassette forms an array of interior cavities in the shapes of wells and channels. The interior cavities create one or more pump chambers and one or more paths to convey fluid. The interior cavities also create one or more valve stations to interconnect the fluid paths with the pump chambers and with each other. The number and arrangement of pump chambers, liquid paths and valve stations can vary. Such a cassette is described in U.S. Pat. No. 5,989,423 and U.S. Pat. No. 5,178,182 both of which, as noted above, are incorporated herein by reference.

In order to accommodate patients with small abdominal cavities, a new process and system is presented that limits the available fill volume. A clinician will be able to select a "low fill mode" from among the modes available on the fluid delivery system. For example, when the low fill mode is on, the fill volumes available will be limited to a range of 60-1000 mL.

Since the fill volumes for the low-fill mode may be as small as 60 mL, it is necessary to achieve a high level of targeting accuracy for these applications. An acceptable range of accuracy may be, for example, +5 mL/−10 mL. It may also be desirable that conforming to this accuracy specification does not take substantially longer than a standard fill.

The targeting accuracy is improved by executing a more intermittent fill during the last phase, in which the incoming flow is stopped one or more times to perform a volume measurement and assess progress. The nominal operation of this fill routine does not result in fills that consistently stop at the low end of the tolerance; instead the nominal operation should fill to the mid-point of the tolerance range. This fill routine especially improves performance for low-fill applications.

Figure 2:
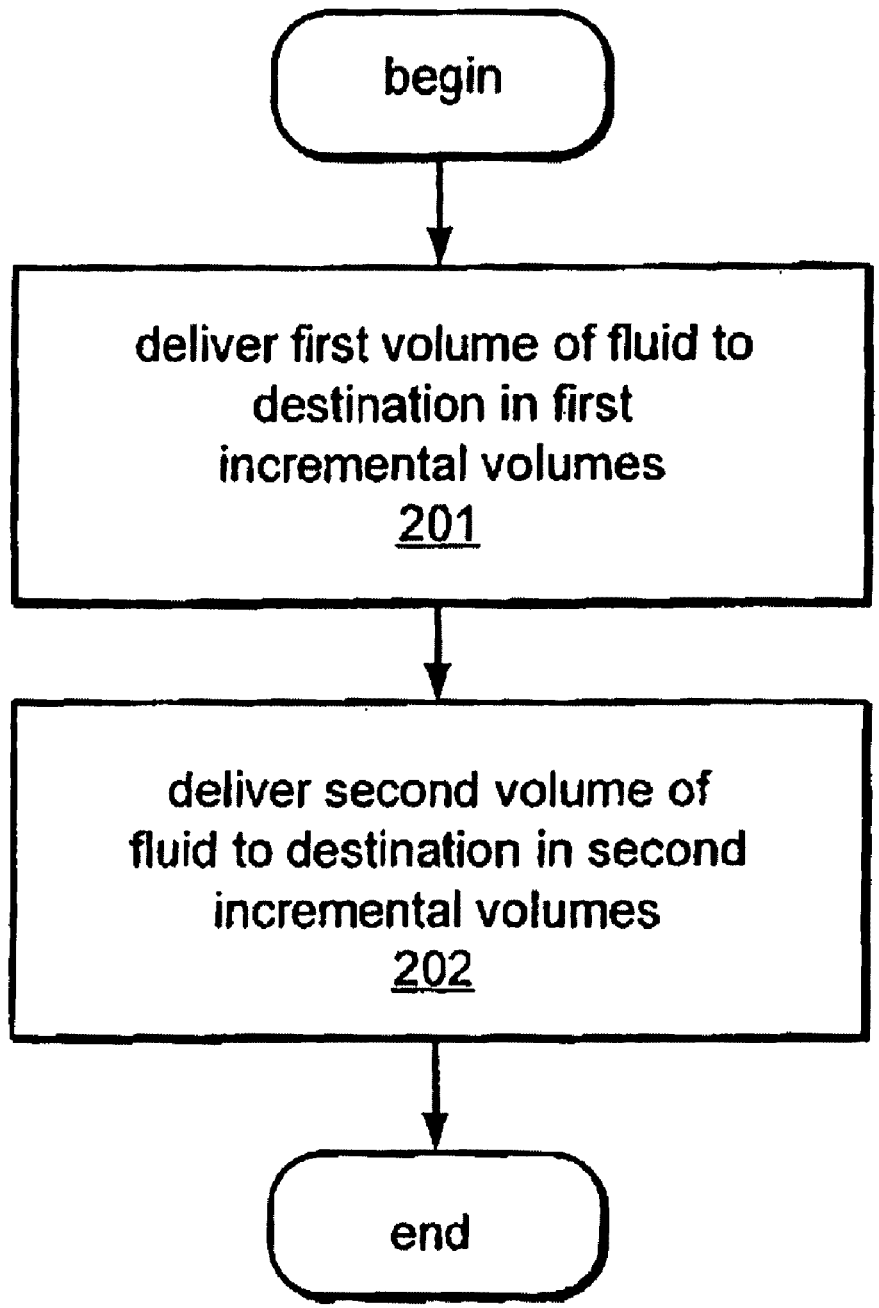
FIG. 2 is a flow chart illustrating a method for delivering a target volume of fluid to a destination in accordance with an embodiment of the invention.
Figure 3:
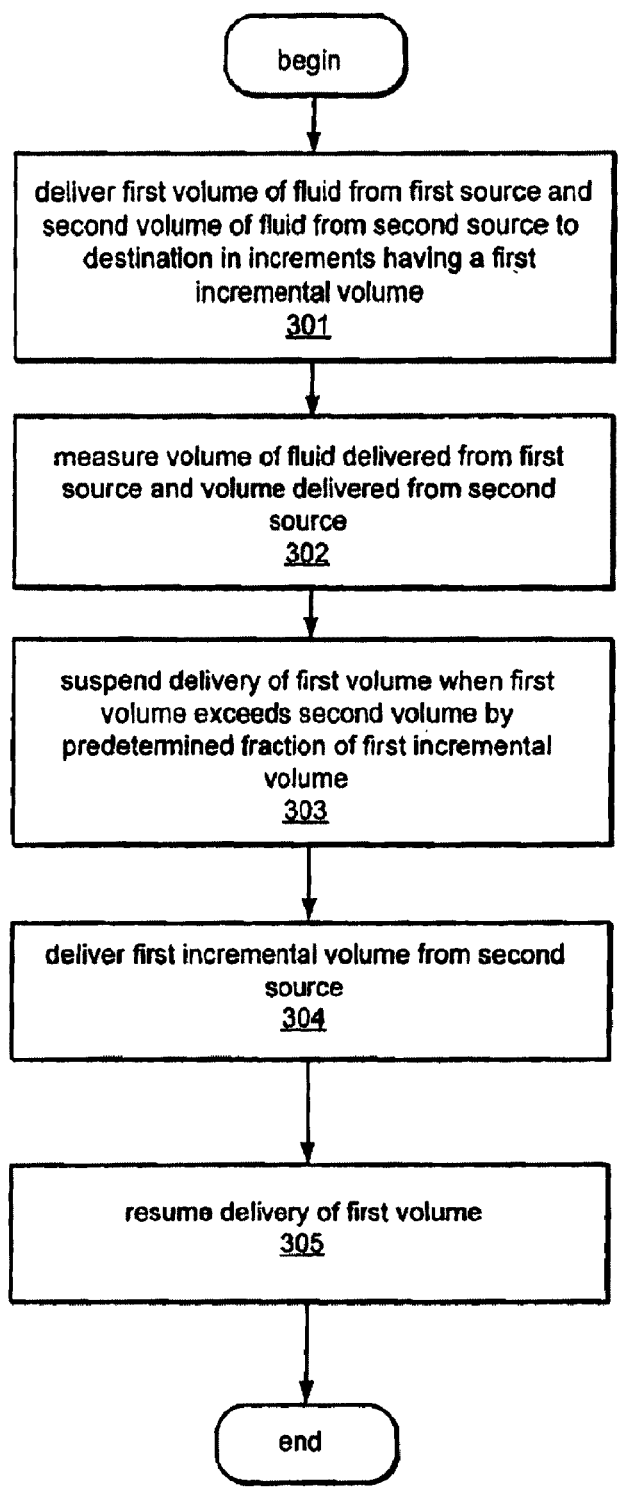
FIG. 3 is a flow chart illustrating a method for simultaneously delivering a target volume of fluid from two sources in a desired ratio to a common destination in accordance with another embodiment of the invention.

FIG. 2 illustrates a method (i.e., a fill routine) for delivering a target volume of fluid to a destination in accordance with one embodiment of the invention. Such a destination may be a human subject, the heating bag 180, a reservoir, a fluid container or pump chamber as illustrated with respect to FIG. 5. The fluid may further be delivered to the human subject parenterally. The method includes delivering 201 a first volume of fluid to the destination in increments each having approximately a first incremental volume. The first volume of fluid is less than the target volume by an amount at least as large as the first incremental volume. For example, if the target volume is 500 mL, the first incremental volume may be 10 to 50 mL. A second volume of fluid is then delivered 202 to the destination in increments each having approximately a second incremental volume. The second incremental volume is less than the first incremental volume, and the sum of the first volume and the second volume is approximately equal to the target volume. For example, if the first incremental volume is 15 mL, then the second incremental volume may be 1 to 3 mL. Note that a plurality of first incremental volumes may be delivered before delivering the second volume. Thus, to achieve a target volume of 500 mL, the first volume may be approximately 485 mL, delivered in thirty or more first incremental volumes of approximately 15 mL each, before the second volume of fluid is delivered in the second incremental volumes of approximately 1 to 3 mL each. Thus, the first volume may approximately equal the target volume minus a finish volume (i.e., the second volumes) and the second incremental volume may be less than the finish volume. For example, the second incremental volume may be one third the finish volume FIG. 3 is a flow chart illustrating a method for simultaneously delivering a target volume of fluid from two sources in a desired ratio, in this case in a 1:1 ratio, to a common destination. Again, such a destination may be a human subject, the heating bag 180, a reservoir, a fluid container or pump chamber. Further, the fluid may be delivered to a human subject parenterally. In a first step, a first volume of fluid from a first source and a second volume of fluid from second source is delivered 301 to the destination in increments each having approximately a first incremental volume. The first volume may be measured in one or more of the pump chambers discussed above in connection with the fluid delivery system of FIG. 1 and in connection with the system FIG. 5. In one embodiment, for example, the volume measurement systems of U.S. Pat. Nos. 4,976,162 and 4,826,482 (incorporated herein above) are employed. The first incremental volume of fluid is substantially less than the target volume. In one embodiment, the first incremental volume is less than one quarter of the target volume. However, the first incremental volume may be less than the target volume by any desired fraction, such as one eighth, one third, one half, two thirds, etc.

After delivery of a first incremental volume of fluid from each of the first source and the second source, the volume of fluid delivered to the destination from the first source and the volume of fluid delivered to the destination from the second source is measured 302. Such delivery may occur simultaneously and such measurements may be performed by the controller 106 by using pressure transducers contained in the fluid control module 104 or other fluid volume measuring apparatuses. Delivery of the first volume of fluid to the destination is suspended 303 when the first volume exceeds the second volume by a fraction, which may be a predetermined fraction, of the first incremental volume. For example, delivery of the first volume of fluid to the destination may be suspended when the first volume exceeds the second volume by approximately one half of the first incremental volume in order to attain a 1:1 one ratio. A first incremental volume of fluid is then delivered 304 to the destination from the second source, and delivery of the first volume of fluid to the destination is resumed 305. It will be appreciated that this process may be adapted for a desired ratio other than one-to-one. In such a case, the fluids from different sources may be delivered by incremental volumes that are the same or that are different from each other. It will also be appreciated that this process may be adapted for use with fluids from more than two different sources.

Figure 4:
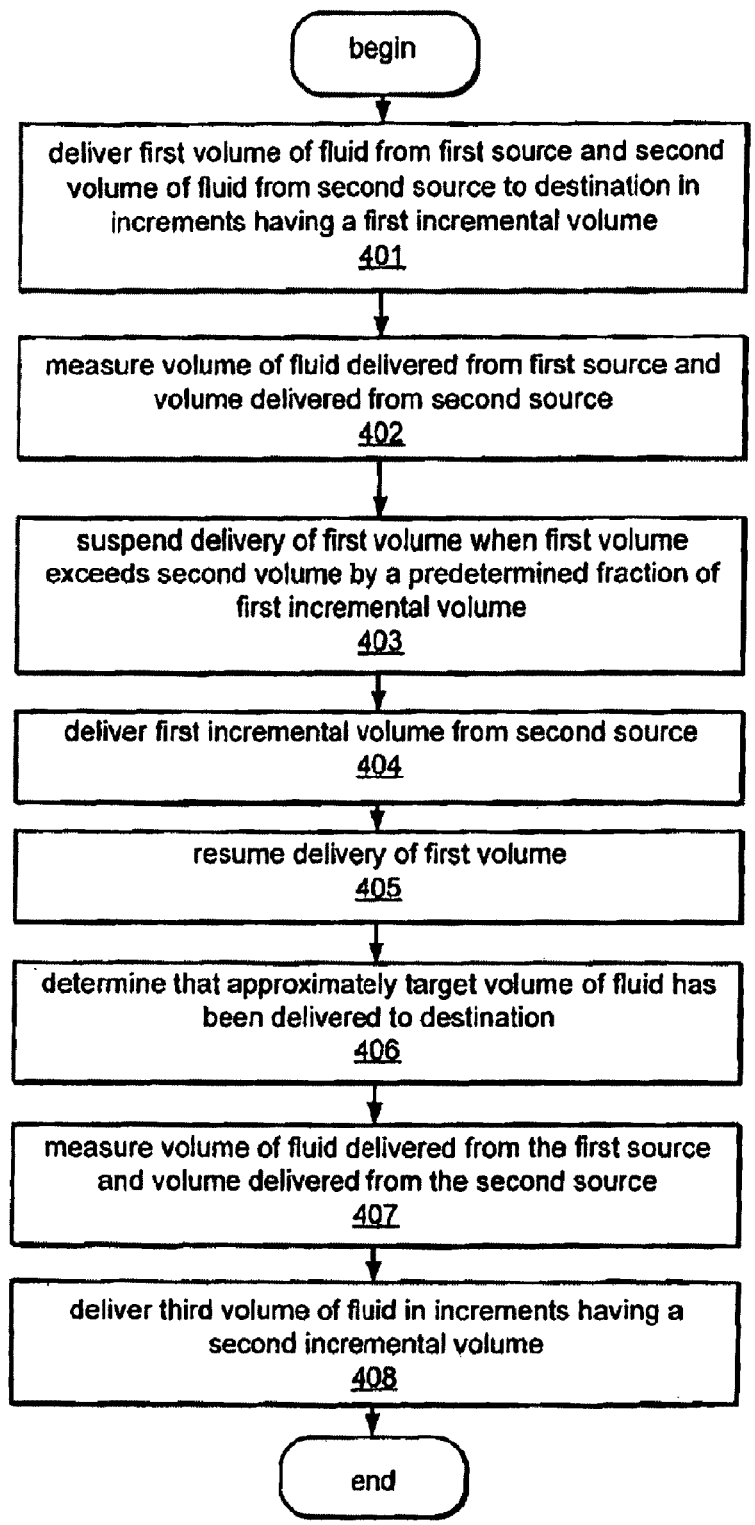
FIG. 4 is a flow chart illustrating a method for simultaneously delivering a target volume of fluid from two sources in a desired ratio to a common destination in accordance with yet another embodiment of the invention.

FIG. 4 is a flow chart illustrating a method for simultaneously delivering a target volume of fluid from two sources in a desired (such as a one-to-one) ratio to a common destination in accordance with yet another embodiment of the invention. The procedure begins in a manner similar to that shown with respect to the embodiment of FIG. 3. That is, a first volume of fluid from a first source and a second volume of fluid from second source is delivered 401 to the destination in increments each having approximately a first incremental volume. The first incremental volume of fluid is less than the target volume. In this case the first incremental volume is less than one quarter of the target volume. However, as noted above the first incremental volume may be less than the target volume by any desired ratio. After delivery of a first incremental volume of fluid from each of the first source and the second source, the volume of fluid delivered to the destination from the first source and the volume of fluid delivered to the destination from the second source is measured 402. Again, such measurements may be performed by the controller 106 by using pressure transducers contained in the fluid control module 104 or other fluid volume measuring means. Delivery of the first volume of fluid to the destination is suspended 403 when the first volume exceeds the second volume by a fraction, which may be a predetermined fraction, of the first incremental volume, in this case by one half the first incremental volume. A first incremental volume of fluid is then delivered 404 to the destination from the second source, and delivery of the first volume of fluid to the destination is resumed 405.

In order to assure that the target volume is delivered in the desired ratio, a determination is made 406 when approximately the target volume of fluid has been delivered to the destination. The volume of fluid delivered to the destination from the first source and the volume of fluid delivered to the destination from the second source are then measured 407. Following this measurement, a third volume of fluid from the source that has delivered a smaller volume of fluid to the destination is delivered 408 in increments each having approximately a second incremental volume. The second incremental volume is less than the first incremental volume. As a result of delivering the third volume of fluid, the sum of the volume of fluid delivered to the destination from the first source and the volume of fluid delivered from the second source are in approximately the desired ratio, in this case a one to one ratio. The first volume and the second volume may each be approximately equal to the target volume minus a finish volume. Similarly, the second incremental volume may be less than the finish volume by any desired fraction. For example, in this embodiment, the second incremental volume may be one third the finish volume.

A system similar to the one described with respect to FIG. 1 may incorporate the processes described above. In this case the fluid control module 104 or other fluid delivery means such as those disclosed in the patents incorporated above, delivers a first volume of fluid to the destination in increments each having approximately a first incremental volume, the first volume of fluid being less than the target volume. The fluid control module 104 will also deliver a second volume of fluid to the destination in increments each having approximately a second incremental volume. Here again, the second incremental volume is less than the first incremental volume, such that the sum of the first volume and the second volume is approximately equal to the target volume. The system additionally includes a valve arrangement, shown generally at 105 for controlling fluid communication between the fluid source or sources and the destination as well as a controller, such as controller 106 or other control means such as a microprocessor or computer. The controller 106 determines the volume of fluid delivered to the destination and for controls the valve arrangement 105 and the fluid control module 104. The controller 106 may also determine when approximately the target volume minus a finish volume of fluid has delivered to the destination. In addition, the fluid control module 104 may measure the volume of fluid delivered to the destination from the first source and the volume of fluid delivered to the destination from the second source. The fluid control module 104 may then deliver a third volume of fluid from the source that has delivered a smaller volume of fluid to the destination in increments each having approximately a second incremental volume.

Figure 5:
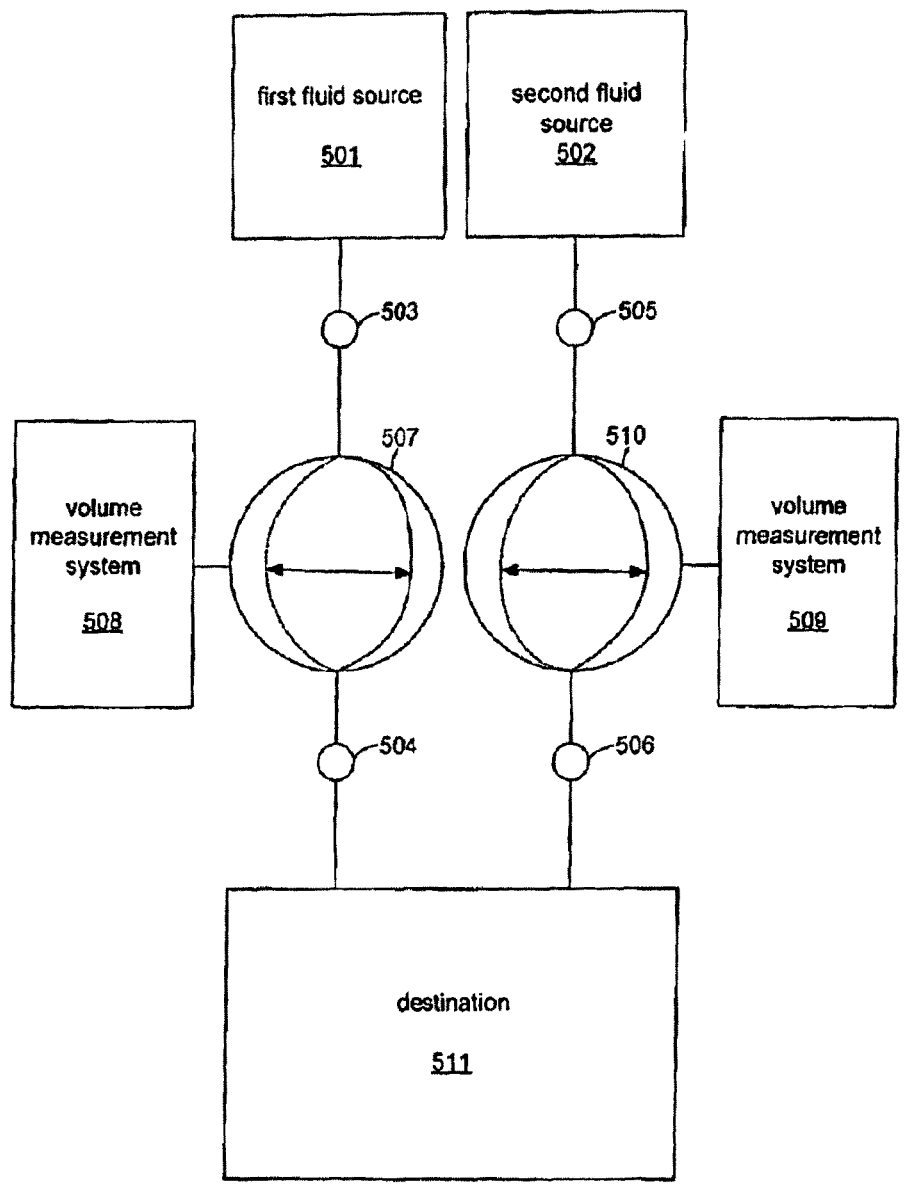
FIG. 5 is a block diagram illustrating one example of a system for employing the methods of FIGS. 3 and 4.

FIG. 5 is a block diagram illustrating an example of a system for employing the methods of FIGS. 3 and 4 above. The system includes a first fluid source 501 and a second fluid source 502. The first fluid source 501 is in fluid communication with a first pump chamber 507 via valve 503 and the second fluid source 502 is in fluid communication with a second pump chamber 510 via valve 505. Pump chamber 507 is also in communication with a volume measurement system 508 and pump chamber 510 is in communication with volume measurement system 509. Alternatively, each pump chamber 507 and 510 may be in communication with a common volume measurement system. Each of the pump chambers 507 and 510 may include flexible membranes as described in the above referenced and incorporated patents. Similarly, each of the volume measurement systems 508 and 509 may include pressure transducers and positive and/or negative pressure reservoirs as are also described in the aforementioned incorporated patents. Each of the pump chambers 507 and 510 is in fluid communication with a destination 511 via valves 504 and 506 respectively. As noted above, the destination 511 may be a human subject, a reservoir, a container, such as a heating bag, or another, perhaps larger, pump chamber.

In accordance with one embodiment, the goal is to separately track the volumes moved from each fluid source 501 and 502 and to ensure that the difference between the fluid delivered from each of the two fluid sources never varies by more than half the volume of a pump chamber. This is achieved by performing in-phase pumping such that both pump chambers 507 and 510 fill and deliver in sync. For example, if each pump chamber holds 15 mL, and it is determined that one pump chamber, for example pump chamber 507, has delivered at least 7.5 mL more fluid to the destination 511 than the other pump chamber 510, then fluid delivery from pump chamber 507 will be suspended while pump chamber 510 performs a catch-up stroke. Such a determination is made by measuring the fluid volumes of each pump chamber 507 and 510 for each pumping stroke via volume measurement systems 508 and 509 respectively. (It should be noted that while each pump chamber 507 and 510 may have a capacity of 15 mL, somewhat less than 15 mL of fluid may be delivered to and by each pump chamber during any single pumping stroke.)

When the target volume (the volume of fluid intended to be delivered to the destination) has been delivered to the destination 511, the pump chamber, perhaps pump chamber 510, that has delivered the most fluid to the destination 511 will stop pumping. The pump chamber which has delivered the least amount of fluid, in this case pump chamber 507, will then switch to a "targeting mode" in which a maximum of 3 mL of fluid is delivered to the destination 511 per pump chamber stroke. This targeting mode insures that a 1:1 ratio (or other desired ratio) between fluid delivered to the destination 511 from the first fluid source 501 and fluid delivered to the destination 511 from the second fluid source 502 is achieved to within approximately plus 2 mL or minus 1 mL.

While the invention has been described in connection with specific embodiments thereof, it will be understood that it is capable of further modification. This application is intended to cover any variation, uses, or adaptations of the invention and including such departures from the present disclosure as come within known or customary practice in the art to which the invention pertains.

What is claimed is:

1. A dialysis system for delivering a target volume of a fluid to a destination, the system comprising:
   a user interface, the user interface configured to allow user selection of a mode from a plurality of user selectable modes, one of the plurality of user selectable modes being a low volume delivery mode which limits the target volume to a predetermined range;
   a flow control module configured to pneumatically act on a delivery set to direct fluid flow through the delivery set, the delivery set having one or more pumping chambers and one or more valve arrangements for controlling fluid communication throughout the system; and
   a controller configured for controlling how much of the fluid is delivered to the destination, controlling the one or more valve arrangements, and controlling the fluid control module, the controller configured for executing each of the plurality of delivery modes,
   wherein when in the low volume delivery mode, the controller is configured to command the flow control module to deliver a first volume of the fluid to the destination and a second volume of the fluid to the destination, the sum of the first volume of the fluid and the second volume of the fluid approximately equal to the target volume, and the controller is configured to command the flow control module to deliver the first volume of the fluid in increments each having approximately a first incremental volume, and for delivering the second volume of the fluid to the destination in increments each having approximately a second incremental volume, the second incremental volume being less than the first incremental volume.

2. The dialysis system of claim 1, wherein the predetermined range is chosen from values between 40 ml and 1200 ml.

3. The dialysis system of claim 1, wherein the predetermined range is between 60 ml and 1000 ml.

4. The dialysis system of claim 1, wherein the one or more pumping chambers comprise a first pumping chamber and a second pumping chamber, each of the first pumping chamber and the second pumping chamber including a flexible membrane.

5. The dialysis system of claim 1, wherein the user interface includes a control pad, the control pad configured for use by a user to navigate and select one of the plurality of user selectable modes.

6. The dialysis system of claim 5, wherein the control pad includes a key or a keypad.

7. The dialysis system of claim 1, wherein the user interface includes a display.

8. The system of claim 1, wherein the destination is a mammalian subject.

9. The system of claim 1, wherein the destination is a peritoneal cavity of a mammalian subject.

10. The system of claim 1, wherein the destination is an anatomical cavity of a mammalian subject.

11. A dialysis system for delivering a target volume of a fluid to a destination, said system comprising:
a flow control module configured to act upon a delivery set to deliver the fluid; and
a controller configured to control the flow control module in each of a plurality of delivery modes, the delivery modes being selectable via an interface configured to allow a selection of a desired delivery mode from the plurality of delivery modes, the plurality of delivery modes including a low volume delivery mode,
wherein when in the low volume delivery mode, the controller is configured to command the flow control module to deliver a first volume of the fluid to the destination and a second volume of the fluid to the destination, the sum of the first volume of the fluid and the second volume of the fluid approximately equal to the target volume, the controller is configured to command the flow control module to deliver the first volume of the fluid in increments each having approximately a first incremental volume, and for delivering the second volume of the fluid to the destination in increments each having approximately a second incremental volume, the second incremental volume being less than the first incremental volume.

12. The system of claim 11, wherein the flow control module is configured to pneumatically act upon the delivery set.

13. The system of claim 11, wherein the flow control module includes at least one pressure reservoir.

14. The system of claim 13, wherein the flow control module includes at least a positive pressure reservoir and a negative pressure reservoir.

15. The system of claim 11, wherein the delivery set includes a cassette.

16. The system of claim 11, wherein the delivery set includes a first pumping chamber and a second pumping chamber.

17. The system of claim 11, wherein the delivery set includes a valve arrangement for controlling fluid communication throughout the system.

18. The system of claim 17, wherein the controller is further configured for controlling the valve arrangement.

19. The system of claim 11, wherein the controller is configured for controlling how much of the fluid is delivered to the destination.

20. The system of claim 11, wherein the low volume delivery mode limits the target volume to a predetermined range.

21. The system of claim 20, wherein the predetermined range is chosen from values between 40 ml and 1200 ml.

22. The system of claim 20, wherein the predetermined range is 60 ml-1000 ml.

23. The system of claim 11, wherein the interface includes a control pad, the control pad configured for use by a user to navigate and select one of the plurality of selectable modes.

24. The system of claim 23, wherein the control pad includes a key or keypad.

25. The system of claim 11, wherein the interface includes a display.

26. The system of claim 11, wherein the dialysis system is a peritoneal dialysis system.

27. The system of claim 11, wherein the system measures volume delivered with a volume measurement system.

28. The system of claim 27, wherein the volume measurement system includes a pressure transducer.

29. The system of claim 11, wherein the system further comprises one or more pressure transducers in the flow control module to provide pressure data allowing the controller to measure volume delivered.

30. A dialysis system for delivering a target volume of a fluid to a destination, the system comprising:
a flow control module configured to pneumatically act on a delivery set to direct fluid flow through the delivery set, the delivery set having at least a first pumping chamber having a first chamber volume, a second pumping chamber having a second chamber volume, and a valve arrangement for controlling fluid communication throughout the system;
a controller configured for controlling how much of the fluid is delivered to the destination, controlling the valve arrangement, and controlling the fluid control module, the controller configured to operate in:
a first mode to command the flow control module to conduct a number of pumping strokes to pump the fluid from the first or the second pumping chamber, each pumping stroke delivering approximately the respective volume of the first pumping chamber or the second pumping chamber; and
a targeting mode after completion of the first mode, the targeting mode to command the flow control module to perform one or more targeting strokes, each targeting stroke delivering a predetermined portion of the respective volume of the first pumping chamber or the second pumping chamber;
wherein the predetermined portion delivered by each targeting stroke is less than the volume delivered with a pumping stroke.

31. The system of claim 30, wherein the system measures volume delivered from the first pumping chamber and the second pumping chamber with a volume measurement system.

32. The system of claim 31, wherein the volume measurement system includes a pressure transducer.

33. The system of claim 30, wherein the flow control module includes one or more pressure reservoir.

34. The system of claim 33, wherein the flow control module includes at least a positive pressure reservoir and a negative pressure reservoir.

35. The system of claim 30, wherein the destination is a peritoneal cavity.

36. The system of claim 30, wherein the first mode is further configured to conduct the pumping strokes such that each of the first pumping chamber and the second pumping chamber fill and deliver in sync.

37. The system of claim 30, wherein the controller is further configured to monitor a cumulative delivery volume and switch from the first mode to the targeting mode upon determination that the cumulative volume exhibits a predetermined characteristic.

38. The system of claim 37, wherein the controller is further configured to separately measure volume pumped through each of the first pumping chamber and the second pumping chamber.

39. The system of claim 38, wherein upon the determination that the cumulative volume exhibits the predetermined characteristic, the flow control module begins performing targeting strokes on whichever of the first or the second pumping chamber has delivered the least amount of the fluid.

40. The system of claim 37, wherein the predetermined characteristic of the cumulative volume is a characteristic in which the cumulative volume is within a predetermined range of the target volume.

41. The system of claim 30, wherein the first pumping chamber and the second pumping chamber each comprise a flexible membrane.

42. The system of claim 30, wherein the system is a peritoneal dialysis system.

43. The system of claim 30, wherein the system further comprises a volume measuring means, the volume measuring means configured to measure volume delivered from the first pumping chamber and the second pumping chamber.

44. A dialysis system for delivering a target volume of a fluid to a destination, the system comprising:
a flow control module configured to act on a delivery set to deliver the fluid;
a controller configured for controlling the fluid control module, the controller configured to operate in:
a first mode to command the flow control module to conduct a number of pumping strokes to pump the fluid from a first pumping chamber or a second pumping chamber of the delivery set, each pumping stroke delivering approximately the respective volume of the first pumping chamber or the second pumping chamber, the first mode configured to monitor a cumulative delivery volume and switch to a targeting mode upon determination that the cumulative volume exhibits a predetermined characteristic;
wherein the targeting mode commands the flow control module to perform one or more targeting strokes until the target volume has been approximately delivered, each targeting stroke delivering a predetermined portion of the respective volume of the first pumping chamber or the second pumping chamber, the predetermined portion delivered by each targeting stroke being less than the volume delivered with a pumping stroke.

45. The system of claim 44, wherein the one or more targeting strokes is performed on a single pump chamber of the first pump chamber and the second pump chamber.

46. The system of claim 45, wherein the single chamber of the first pumping chamber and the second pumping chamber is the pumping chamber to have delivered the least fluid.

47. The system of claim 44, wherein the predetermined characteristic of the cumulative volume is a characteristic in which the cumulative volume is within a predetermined range of the target volume.

48. The system of claim 44, wherein the cumulative volume delivered by the one or more targeting strokes is less than the cumulative volume delivered by the number of pumping strokes.

49. The system of claim 44, wherein the flow control module pneumatically acts upon the delivery set to deliver the fluid.

50. The system of claim 44, wherein the flow control module includes a pressure reservoir.

51. The system of claim 44, wherein the flow control module includes a positive pressure reservoir and a negative pressure reservoir.

52. The system of claim 44, wherein the system is configured to measure volume delivered from the first pumping chamber and the second pumping chamber via a volume measurement system.

53. The system of claim 52, wherein the volume measurement system includes a pressure transducer.

54. The system of claim 44, wherein when in the first mode the controller is configured to conduct the number of pumping strokes such that each of the first pumping chamber and the second pumping chamber fill and deliver in sync.

55. The system of claim 44, wherein the delivery set includes a valve arrangement for controlling fluid communication throughout the system.

56. The system of claim 55, wherein the controller is further configured for controlling the valve arrangement.

57. The system of claim 44, wherein the controller is configured for controlling how much of the fluid is delivered to the destination.

58. A fluid pumping system for delivering a predetermined volume to a destination, said system comprising:
a user interface to input a predetermined volume within a range, wherein a sub range of the range corresponds to a low-volume mode;
a cassette with one or more pumping chambers configured to operate in accordance with a selected input;
a volume measurement device in operative communication with the one or more pumping chamber and configured to estimate successive volumes of fluid that flow through the pumping chambers;
a controller configured to compare a sum of the successive volumes of fluid flowing through the pumping chambers with the predetermined volume, wherein said comparison determines whether the controller directs the operation of a single one of the one or more pumping chambers, such that said single pumping chamber delivers the fluid in a volume that is less than each of said successive volumes of fluid in order to deliver said predetermined volume to said destination.

59. The system according to claim 58, wherein the comparison is a function of the predetermined volume.

60. The system according to claim 59, wherein the comparison is whether another successive volume is greater than a remaining fluid to be infused to achieve the predetermined volume.

* * * * *